United States Patent
Ernst

(10) Patent No.: US 11,839,670 B2
(45) Date of Patent: *Dec. 12, 2023

(54) METHOD AND APPARATUS FOR PREVENTING PLAQUE, CALCULUS, AND HARD DEPOSITS IN BODY CAVITIES AND THE MOUTH

(71) Applicant: Maurice Moshe Ernst, Jerusalem (IL)

(72) Inventor: Maurice Moshe Ernst, Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/152,814

(22) Filed: Jan. 20, 2021

(65) Prior Publication Data

US 2021/0237705 A1 Aug. 5, 2021

Related U.S. Application Data

(63) Continuation of application No. 16/684,166, filed on Nov. 14, 2019, now Pat. No. 11,066,058, which is a continuation of application No. 14/970,561, filed on Dec. 16, 2015, now Pat. No. 10,688,027.

(60) Provisional application No. 62/194,310, filed on Jul. 20, 2015.

(51) Int. Cl.

| | |
|---|---|
| *A61K 8/19* | (2006.01) |
| *A61C 19/06* | (2006.01) |
| *A61K 6/20* | (2020.01) |
| *A61K 6/849* | (2020.01) |
| *B60H 1/32* | (2006.01) |
| *B60T 13/72* | (2006.01) |
| *F02D 13/02* | (2006.01) |
| *F02D 41/08* | (2006.01) |
| *F02D 41/12* | (2006.01) |
| *A61C 7/16* | (2006.01) |
| *A61K 8/27* | (2006.01) |
| *A61Q 11/00* | (2006.01) |

(52) U.S. Cl.
CPC .............. *A61K 8/19* (2013.01); *A61C 7/16* (2013.01); *A61C 19/063* (2013.01); *A61K 6/20* (2020.01); *A61K 6/849* (2020.01); *A61K 8/27* (2013.01); *A61Q 11/00* (2013.01); *B60H 1/3205* (2013.01); *B60T 13/72* (2013.01); *F02D 13/0223* (2013.01); *F02D 41/083* (2013.01); *F02D 41/12* (2013.01); *A61K 2800/5922* (2013.01); *A61K 2800/884* (2013.01)

(58) Field of Classification Search
CPC .......... A61K 6/0017; A61K 8/19; A61K 8/27; A61K 8/849; A61C 7/16
USPC ............... 433/201, 217.1, 219; 424/435
See application file for complete search history.

(56) References Cited

U.S. PATENT DOCUMENTS

| | | |
|---|---|---|
| 9,114,197 B1 | 8/2015 | Dehnad |
| 2004/0005277 A1 | 1/2004 | Wilson |
| 2004/0234462 A1 | 11/2004 | Algar |
| 2006/0073174 A1 | 4/2006 | Moro |
| 2009/0324662 A1 | 12/2009 | Kutsch |

FOREIGN PATENT DOCUMENTS

WO 201409868 6/2014

OTHER PUBLICATIONS

Marsh, "Dental plaque as biofilm and a microbial community—implications for health and disease," in BMC Oral Health 2006, 6(Suppl 1):S14, Published Jul. 10, 2006.
Kenney, et al., "Oxidation Reduction Potential of Developing Plaque, Peridontal Pockets and Gingival Sulcii", in Journal of Periodontology, Nov. 1969, vol. 40, No. 11, pp. 630-633.

*Primary Examiner* — Walter E Webb

(57) ABSTRACT

A method and apparatus, for treating plaque and calculus in the mouth cavity—particularly on teeth are disclosed. The apparatus—and accordingly the method—is comprised of introducing at least one first-component comprising a material with a redox potential for preventing anions precipitation; and introducing at least one second-component comprising a material with a redox potential for preventing cations precipitation.

8 Claims, 2 Drawing Sheets

METHOD AND APPARATUS FOR PREVENTING PLAQUE, CALCULUS, AND HARD DEPOSITS IN BODY CAVITIES AND THE MOUTH

CROSS-REFERENCES TO RELATED APPLICATIONS

This application is a Continuation of commonly owned U.S. patent application Ser. No. 16/884,166, entitled: Method and Apparatus for Preventing Plaque, Calculus, and Hard Deposits in Body Cavities and the Mouth, filed on May 27, 2020, now U.S. Pat. No. 10,898,417, which of is a Continuation of commonly owned U.S. patent application Ser. No. 14/970,561, entitled: Method and Apparatus for Preventing Plaque, Calculus, and Hard Deposits in Body Cavities and the Mouth, filed on Dec. 16, 2015, now U.S. Pat. No. 10,688,027, which is related to and claims priority from commonly owned U.S. Provisional Patent Application Ser. No. 62/194,310, entitled: Method and System For Prevention and Removal of Hard Deposits in Body Cavities and Mouth, filed on Jul. 20, 2015, the disclosures of these three patent applications are incorporated by reference in their entireties herein.

TECHNICAL FIELD

The present invention relates to the field of treating plaque and calculus in a human body. More specifically, the present invention relates to a method and apparatus for treating plaque and calculus in the human body particularly in the mouth cavity especially on a tooth.

BACKGROUND

Calculus is composed of both inorganic (mineral) and organic (cellular and extracellular matrix) components. The mineral proportion of calculus ranges from approximately 40-60%, depending on its location in the dentition. Calculus consists primarily of calcium phosphate crystals organized into four principal mineral phases: octacalcium phosphate, hydroxyapatite, whitlockite, and brushite. The organic component of calculus is approximately 85% cellular and 15% extracellular matrix. Cell density within dental plaque and calculus is very high, consisting of an estimated 200,000,000 cells per milligram. The cells within calculus are primarily bacterial, but also include at least one species of archaea (*Methanobrevibacter oralis*) and several species of yeast (e.g., *Candida albicans*). The organic extracellular matrix in calculus consists primarily of proteins and lipids (fatty acids, triglycerides, glycolipids, and phospholipids) as well as extracellular DNA. Trace amounts of host, dietary, and environmental micro-debris are also found within calculus, including salivary proteins, plant DNA, milk proteins, starch granules, textile fiber, and smoke particles.

Sub-gingival calculus (tartar) is composed almost wholly of two components: fossilized anaerobic bacteria whose biologic composition has been replaced by calcium phosphate salts, and calcium phosphate salts that have joined the fossilized bacteria in calculus formations. The initial attachment mechanism and the development of mature calculus formations are based on an electrical charge. Unlike calcium phosphate, the primary component of teeth, calcium phosphate salts exist as electrically unstable ions. The following minerals are detectable in calculus by X-ray diffraction: brushite ($CaHPO_4 \cdot 2H_2O$), Octa calcium phosphate ($Ca_8H_2(PO_4)_6 \cdot 5H_2O$), magnesium-containing whitlockite ($Ca_9(MgFe)(PO_4)_6PO_3OH$), and carbonate-containing hydroxyapatite (approximately $Ca_5(PO_4)_3(OH)$ but containing some carbonate).

The reason fossilized bacteria are initially attracted to one part of the sub-gingival tooth surface over another is not fully understood; once the first layer is attached, ionized calculus components are naturally attracted to the same places due to electrical charge. The fossilized bacteria pile on top of one another, in a rather haphazard manner. All the while, free-floating ionic components fill in the gaps left by the fossilized bacteria. The resultant hardened structure can be compared to concrete; with the fossilized bacteria playing the role of aggregate, and the smaller calcium phosphate salts being the cement. The once purely electrical association of fossilized bacteria then becomes mechanical, with the introduction of free-floating calcium phosphate salts. The "hardened" calculus formations are at the heart of periodontal disease and treatment.

As a summary, in general dental calculus (Sub-gingival) consists of inorganic (70% to 90%) and organic components. The inorganic portion consists mainly (70-80%) of calcium phosphate, $Ca_3(PO_4)_2$; calcium carbonate (3-5%), $CaCO_3$; and traces of magnesium phosphate, $Mg_3(PO_4)_2$, and other metals. The percentage of inorganic constituents in calculus is similar to that in other calcified tissues of the body.

The principal inorganic components are calcium, about 40%; phosphorus, about 20%; carbon dioxide, about 2%; magnesium, about 1%; and trace amounts of sodium, zinc, strontium, bromine, copper, manganese, tungsten, gold, aluminum, silicon, iron, and fluorine.

At least two thirds of the inorganic component are crystalline in structure. The four main crystal forms and their percentages are as follows:

Hydroxyapatite, approximately 58%
Magnesium whitlockite, approximately 21%
Octacalcium phosphate, approximately 12%
Brushite, approximately 9%

The organic content of dental calculus (Sub-gingival) consists of a mixture of: protein-polysaccharide complexes, epithelial cells, leukocytes, and various types of microorganisms. 2-10% of the organic component are carbohydrate, which consists of galactose, glucose, glucuronic acid, galactosamine, and sometimes, galacturonic acid, and Glucosamine.

There are few effective ways to prevent the buildup of calculus: through daily tooth brushing and flossing (which removes dental plaque) and regular cleaning visits based on a schedule recommended by the dental health care provider. Calculus accumulates more easily in some individuals, requiring more frequent brushing and dental visits. Smoking and diabetes are external factors that facilitate the accumulation of calculus. Toothpaste with an additive ingredient of zinc citrate has been shown to produce reduction in plaque accumulation.

SUMMARY OF THE INVENTION

The present invention is directed to systems and methods for treating-preventing and removal-of hard deposits, organic and inorganic plaque and calculus parts in the body cavities and mouth.

Embodiments of the present invention deploy components that include materials and composite materials, (which include variety of metal ions, metals and variety of cations) into the oral cavity. The material or the composite materials can be insoluble state or solid state; it can be with a single compound (e.g., gold), or a single component material or multiple component material. A single component can be an alloy, made of a multiple component material and can made of two different metals (e.g., copper and zinc), or can be in a composite form (e.g., a composite material that is made from a mixture of multiple compounds), which can be effective in reduction or oxidation. For example, a result of an oxidation half reaction by putting together solid Zinc and solid copper, in different Molar quantitative ratios. The material or the composite materials, once in the oral cavity, will change the redox (Reduction/Oxidation) potentials of the precipitants to a non-solid state. Accordingly, the potential difference prevents the formation of the plaque and calculus and the dental plaque and calculus. This process may also reverse the previous precipitants, and dissolve existing deposits. Optionally, the material or the composite materials can dissolve in body fluids (e.g., gingival fluids or saliva) or can be in touch with them to create the right redox potentials, which will prevent the dental plaque and calculus.

According to the present invention, different types of mouth application techniques can achieve dental plaque and calculus prevention process, using changing the redox potential of the precipitants, such as placement in adhesives or prosthetic materials, being adhesive or mechanically attached to the teeth by dental compounds (that include metals or composite materials or both) or by direct or indirect mechanical attachments. It includes a sticker placed on the teeth, ortho brackets, mouth washes, slow release chips in the gingivae, e.g., "perio chip", toothbrushes with release solution, or a slow release compound embedded in a material that may have a control chip with a control feature that regulates the release flow according to concentrations in the "electronic solution".

According to the present invention, there is provided a method for treating plaque and calculus on the teeth. The method comprises of (a) introducing at least one first-component comprising a material with a redox potential for preventing anions precipitation; and (b) introducing at least one second-component comprising a material with a redox potential for preventing cations precipitation.

According to a preferred embodiment, each of the components is made of at least one material or composite material—organic or inorganic—and wherein the components are packaged in at least one unit to be attached to the teeth or to the gingivae.

According to another preferred embodiment of the method, at least one of the components is an intermediate agent or a catalytic agent, which enhances the prevention of the precipitation.

According to another preferred embodiment of the method, the unit has the capability to release slowly the material or composite materials into the saliva.

According to another preferred embodiment of the method, a controller is added to the unit that is capable to control the release of material or composite materials, according to predetermined criteria.

According to another aspect of the present invention, an apparatus is provided for treating plaque and calculus in the mouth cavity, particularly on teeth, this apparatus is comprised of at least one first-component comprising a material with a redox potential for preventing anions precipitation and at least one second-component comprising a material with a redox potential for preventing cations precipitation wherein these components are designed to be placed inside the mouth cavity and to be in touch with the saliva.

According to a preferred embodiment, the apparatus is provided wherein it is designed to be attached on a tooth and on the gingivae.

According to another preferred embodiment, the apparatus is designed as that capable to release slowly the components' materials.

According to another preferred embodiment, the apparatus further includes a controller operative for controlling the release of the components' materials, according to predetermined criteria.

According to yet another preferred embodiment, the apparatus is provided wherein the components are implemented as an orthodontic bracket and cement—for attaching the bracket to the tooth—wherein the bracket and cement are made of the mentioned materials.

According to yet another aspect of the present invention, it is provided a method for treating plaque and calculus in the human body, the method is comprised of the steps (a) introducing at least one first-component comprising a material with a redox potential for preventing anions precipitation; and (b) introducing at least one second-component comprising a material with a redox potential for preventing cations precipitation.

In a preferred use of the method, each of the components is made of at least one material or composite material—organic or inorganic—and wherein the components are packaged in at least one unit to be located in the under treatment area.

In another preferred use of the method, the unit has the capability to release slowly the material or composite materials in the under treatment area.

In another preferred use of the method, further adding a controller to the unit that is capable to control the release, of the material or composite materials, according to predetermined criteria.

In another preferred use of the method, at least one of the components is intermediate agent or catalytic agent in order to enhance the preventing precipitation.

In another preferred use of the method, using a cathodic protection, to control the oxidation of the components' material surfaces.

In yet another preferred use of the method, the cathodic protection is achieved by using an outside potential source for a short time treatment.

Examples of Implementation

In the principles of electrochemistry, the more positive reduction potential gives a more oxidative agent, the more negative reduction potential, gives more reductive agent and the more positive reduction reaction potential gives more spontaneous reaction.

The main object of the present invention is to prevent precipitation of calculus also known as tartar, which is composed of different types of precipitant compound. Precipitation prevention it means to change the priority of the precipitation reaction by changing the potentials to produce a non-precipitant compound. This can be achieved by producing more positive reduction reaction potential than that of the precipitate to a non-precipitate species. Following are some examples.

$Ca2+(aq)+2e-\rightarrow Ca(s)$. The Standard Potential $E^o$ (volts) of this reaction is −2.76 v (negative). It means that the opposite reaction potential [oxidation of Ca (s) to Ca2+(aq)] is +2.76 v (positive). By providing a non-precipitant stronger oxidation agent than Ca2+(aq), which will not produce the precipitant of Calcium, its prevents the precipitation.

Actually, there are two direction reactions, that means that by adding Calcium (0) metal to the composite the reaction priority is changed.

Mg2+(aq)+2e−→Mg (s). The Standard Potential E° (volts) of this reaction is −2.38 v (negative). It means that the opposite reaction potential [oxidation of Mg (s) to Mg2+ (aq)] is +2.38 v (positive). By providing a non-precipitant stronger oxidation agent than Mg2+(aq), which will not produce the precipitant of Magnesium, the precipitation is prevented. Actually, there are two direction reactions, that means that by adding Magnesium (0) metal to the composite the reaction priority is changed.

By putting together Zinc (metal) with copper salt (Cu+2), the spontaneous reaction is: Cu+2 (aq)+Zn (s)→Cu (s)+Zn2+(aq) with standard potential (E0) of +1.10 v, which gives as a spontaneous reaction. Cu2+(aq)+2e−→Cu (s) with E0 of +0.34 (Positive), and Zn2+(aq)+2e−→Zn (s) with E0 of −0.76 (Negative). The oxidation of Zn (s) is with E0 of +0.76 (Positive). Actually, there are two direction reactions and that mean that by adding Zinc (0) metal to the composite the reaction priority is changed.

When putting together Gold (metal), Common oxidation states of gold include+1 (gold (I) or aurous compounds) and +3 (gold (III) or auric compounds). Gold ions in solution are readily reduced and precipitated as metal by adding any other metal as the reducing agent. The added metal is oxidized and dissolves, allowing the gold to be displaced from solution and be recovered as a solid precipitate. In the case of putting oxidizing agent, it can change the reaction direction of metal gold (in amalgam or other forms) to one of the Gold oxidation states, which will prevent precipitation of other salts. Gold readily dissolves in mercury at room temperature to form a composite such as an amalgam, and forms alloys with many other metals at higher temperatures. These alloys can be produced to modify the hardness and other metallurgical properties, to control melting point or to create exotic colors.

BRIEF DESCRIPTION OF THE DRAWINGS

Attention is now directed to the drawings, where like reference numerals or characters indicate corresponding or like components. In the drawings.

DETAILED DESCRIPTION OF THE PREFERRED EMBODIMENTS

Figure 1:
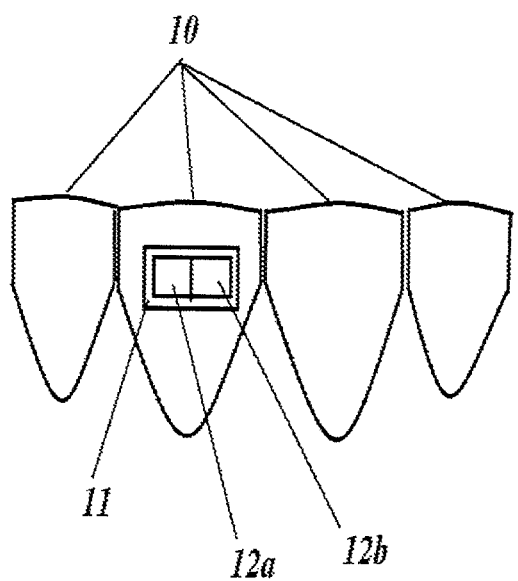
FIG. 1 is an apparatus in accordance with the present invention in an example operation; and, FIG. 2 is an alternative apparatus in accordance with the present invention.

Attention is now directed to FIG. 1. The apparatus 11 is shown, for example, as a sticker that is attached to one or more teeth 10, typically on the inner side. The teeth 10 may include, for example, one of the lower incisors. The illustrated sticker 11 is with two units, a first unit 12a, which is made of an alloy of gold, zinc, copper and mercury, and a second unit 12b, which is made of gold salts, platinum salts, zinc salts, copper salts and magnesium salts. The materials of the units react as described above and treat plaque and calculus-which prevents precipitation and reverse the existing precipitations.

Figure 2:
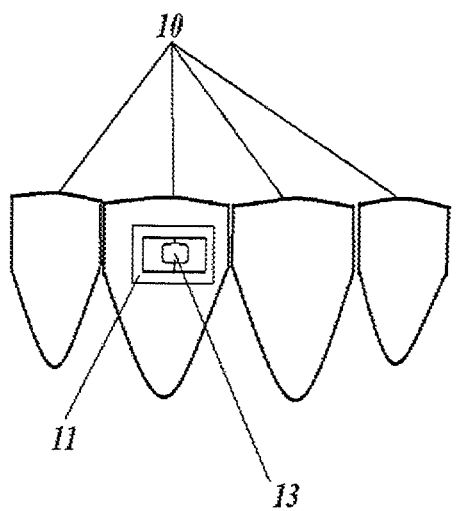

FIG. 2 shows the apparatus 11 where a controller 13 has been added to the apparatus 11. The controller 13 functions in cases that the materials are slowly released, the releasing rate can be controlled by the controller 13 according to predetermined criteria. In a preferred embodiment the controller 13 can use cathodic protection methods.

While the present invention has been described, so as to enable one of skill in the art to practice the present invention, the preceding description is intended to be exemplary only. It should not be used to limit the scope of the invention, which should be determined by reference to the following claims.

The invention claimed is:

1. A method for treating plaque and calculus in the oral cavity comprising:
    providing an apparatus comprising:
        a first inner side and a second outer side, the first inner side comprising an adhesive or a mechanical attachment and the second outer side comprising at least one first unit and at least Van one second unit;
        the at least one first unit comprising a material with a redox potential for inhibiting anion precipitation; and,
        the at least one second unit comprising a material with a redox potential for inhibiting cation precipitation, wherein once in the oral cavity, the redox potentials of the materials change to produce non-precipitant compounds; and,
    placing the apparatus at the first inner side on at least one tooth and/or gingavae.

2. The method of claim 1, wherein the at least one first unit and the at least one second unit release their materials over a predetermined time upon contact with at least one of saliva or gingival fluid in the mouth cavity.

3. The method of claim 2, additionally comprising: a controller for controlling the release of the materials.

4. The method of claim 1, wherein the material of the at least one first unit includes metals.

5. The method of claim 4, wherein the metals are selected from the group consisting of: gold, zinc, copper, mercury, and alloys thereof.

6. The method of claim 1, wherein the material of the at least one second unit includes metal salts.

7. The method of claim 6, wherein the metal salts include at least one metal, the metal selected from the group consisting of gold, platinum, zinc, copper, and magnesium.

8. The method of claim 1, wherein the adhesive or mechanical attachment includes a sticker for adhering to at least one tooth and/or the gingivae.

* * * * *